United States Patent [19]
Beissner et al.

[11] Patent Number: 6,135,627
[45] Date of Patent: Oct. 24, 2000

[54] METHOD, APPARATUS, AND ARTICLE OF MANUFACTURE FOR MODELING EDDY CURRENT PROBES AND SIMULATING EDDY CURRENT EXAMINATIONS

[75] Inventors: Robert E. Beissner; Edith A. Creek, both of San Antonio, Tex.

[73] Assignee: Southwest Research Institute, San Antonio, Tex.

[21] Appl. No.: 08/870,424

[22] Filed: May 28, 1997

[51] Int. Cl.$^7$ ........................................ G06F 15/00
[52] U.S. Cl. ............................................. 364/578
[58] Field of Search ................................. 364/578, 512; 702/34, 35, 38; 324/222, 239, 240

[56] References Cited

U.S. PATENT DOCUMENTS

| | | |
|---|---|---|
| 4,064,452 | 12/1977 | Toth . |
| 4,430,615 | 2/1984 | Calvert . |
| 4,578,643 | 3/1986 | Junker et al. . |
| 5,202,837 | 4/1993 | Coe et al. . |
| 5,336,997 | 8/1994 | Anim-Appiah et al. . |
| 5,453,689 | 9/1995 | Goldfine et al. ........................ 324/239 |
| 5,483,160 | 1/1996 | Gulliver et al. . |

OTHER PUBLICATIONS

Allen P. Mills, Jr., "Method for measuring magnetic moments with precision", Journal of Applied Physics, vol. 45, Dec. 12, 1974, pp. 5440–5442.

R. E. Beisssner, "Boundary element model of eddy current flaw detection in three–dimensions", J. Appl. Phys., vol. 60, Jul. 1, 1986, pp. 352–356.

W. Scott Dunbar, "The volume integral method of eddy current modeling", Journal of Nondestructive Evaluation, vol. 5, 1985, pp. 9–14.

David McA. McKirdy, "Recent improvements to the application of the volume integral method of eddy current modeling", Journal of Nondestructive Evaluation, vol. 8, 1989, pp. 45–52.

C. V. Dodd et al., "Analytical solutions to eddy–current probe–coil problems", J. Appl. Phys., vol. 39, May 1968 pp. 2829–2838.

R. E. Beissner et al., "Theory of eddy currents induced by a nonsymmetric coil above a conducting half–space", J. Appl. Phys., vol. 56, Jul. 15, 1984, pp. 448–454.

S. K. Burke, "Impedance of a horizontal coil above a conducting half–space", J. Phys. D: Appl. Phys., vol. 19, 1986, pp. 1159–1173.

S. K. Burke, "A semi–empirical model for eddy–current NDE using ferrite–cored probes", Nondestructive Testing and Evaluation, vol. 6, 1992, pp. 267–277.

S. K. Burke, A benchmark problem for computation of $\Delta Z$ in eddy–current nondestructive evaluation (NDE), Journal of Nondestructive Evaluation, vol. 7, 1988, pp. 35–41.

Rasolonjanahary et al., "Study of Eddy Currents Non Destructive Testing System in Riveted Assemblies", pp. 1585–1588, IEEE Transactions on Magnetics, vol. 32, No. 3, May 1996.

Pave et al., "Optimal Design of Eddy Current Testing Probe Using Fluxset Magnetic Field Sensors", pp. 1597–1600, IEEE Transactions on Magnetics, vol. 32, No. 3, May 1996.

*Primary Examiner*—Kevin J. Teska
*Assistant Examiner*—Douglas W. Sergent
*Attorney, Agent, or Firm*—Venable; Robert Kinberg; Michael A. Sartori

[57] ABSTRACT

A method, an apparatus, and an article for manufacture for modeling an eddy current probe and simulating an eddy current examination of a material is presented. An eddy current probe model of the eddy current probe is produced using a first numerical technique, such as the finite element method. A magnetic vector potential for a surface is obtained from the eddy current probe model, and is transformed. A material model of the material is produced using a second numerical technique, such as the volume integral method or the boundary element method. An examination of the material is simulated using the transformed magnetic vector potential and the material model.

15 Claims, 5 Drawing Sheets

METHOD, APPARATUS, AND ARTICLE OF MANUFACTURE FOR MODELING EDDY CURRENT PROBES AND SIMULATING EDDY CURRENT EXAMINATIONS

BACKGROUND OF THE INVENTION

The present invention relates generally to eddy current examinations of a material and, more particularly, to a method, an apparatus, and an article of manufacture for modeling eddy current probes and simulating eddy current examinations of a material.

Modeling complex eddy current probes and simulating eddy current examinations of a material is critical to the design of eddy current inspection systems. The increasing demand for specialized eddy current probes has created a need for the modeling of more complex eddy current probes and the simulation of more complex eddy current examinations.

Eddy current examination simulations are a valuable tool in the design and optimization of eddy current probes. A simulated eddy current examination generates the response of the eddy current probe for a series of scans of a material. Further, the simulated eddy current examination provides insight into the physics of the interaction between the material, a flaw in the material, and the eddy current probe. With simulated eddy current examinations, improved eddy current probe design for increasingly specialized eddy current examinations can be accomplished.

Three different numerical techniques are commonly used to model eddy current probes and to simulate eddy current examinations: the finite element method ("FEM"), the volume integral method ("VIM"), and the boundary element method ("BEM").

Of the three numerical techniques, the FEM is the most general numerical technique with the capability of modeling an eddy current probe of any geometry and made with any material. Computer software packages for generating models of an eddy current probe using the FEM are commercially available, and one such package is the "EMAS" package developed by Ansoft Corp., Pittsburgh, Pa. For conventional use of the FEM, a volume mesh is generated which includes the eddy current probe, the material to be examined, which typically includes a flaw, and the surrounding fluid, which is typically air. The field solution is determined for every point in the space of the volume mesh.

The output impedance of the modeled eddy current probe is determined from the field solution and is a single value for the eddy current probe at a fixed location with respect to the material, and more particularly with respect to the flaw in the material. In order to obtain the output impedance of the modeled eddy current probe for a scan across the material, a new volume mesh and a new field solution must be determined for each point in the scan. Further, to obtain a simulated eddy current examination of the material, a series of scans across the material is required, and a new volume mesh and a new field solution must be determined for each point in each scan. This is a very time consuming procedure.

Because the volume mesh generation is so time intensive, it is impractical to generate a simulated eddy current examination of the material with the FEM for a scan across the material, and impractical for a series of scans across the material. Instead, the FEM is used for understanding the physics of the interaction between the eddy current probe, the material, and, if present, the flaw in the material.

In addition to the FEM, the VIM and the BEM are two numerical techniques which can be adapted to generate an eddy current examination of a material. See W. S. Dunbar, "The Volume Integral Method of Eddy Current Modeling," J. Nondestructive Eval., 5:9–14 (1985); D. M. McKirdy, "Recent Improvements to the Application of the Volume Integral Method of Eddy Current Modeling," J. Nondestructive Eval., 8:45–52 (1989); R. E. Beissner, "Boundary Element Model of Eddy Current Flow Detection in Three Directions," J. Appl. Phys., 60:352–356 (1986). Computer software packages are commercially available for developing models using the VIM and BEM numerical techniques. For example, the "VIC-3D" by Sabbagh Associates, Inc., Bloomington, Indiana is a package for modeling using the VIM, and "FARADAY" by Integrated Engineering Software, Winnipeg, Canada is a package for modeling using the BEM.

Conventional formulations for the VIM and the BEN depend on the coil dimensions and current of the eddy current probe. Typically, solutions or equivalent analytical expressions can be used to determine the magnetic potential field produced by the coil of the eddy current probe. See C. V. Dodd and W. E. Deeds, "Analytical Solutions to Eddy-Current Probe-Coil Problems," J. Appl. Phys., 39:2829–2838 (1968); R. E. Beissner and M. J. Sablik, "Theory of Eddy Currents Induced by a Nonsymmetric Coil Above a Conducting Half-Space," J. Appl. Phys., 56:448–454 (1984); and S. K. Burke, "Impedance of a Horizontal Coil Above a Conducting Half-Space," J. Phys. D: Appl. Phys., 19:1159–1173 (1986). This makes it difficult to model complex eddy current probe geometries and eddy current probe arrays, and impossible to model eddy current probes with ferrite cores or with shielding of any type.

SUMMARY OF THE INVENTION

It is an object of the present invention to provide flexibility in the design of eddy current probes, including a single eddy current probe having complex geometry and made of any material, and including an array of eddy current probes having any complex geometry and made of any materials.

Another object of the present invention is to simulate quickly and efficiently the examination using an eddy current probe, or an array of eddy current probes, of any material, which may or may not include a flaw or a series of flaws.

The above objects and advantages of the present invention are achieved by a method, an apparatus, and an article of manufacture for modeling eddy current probes and simulating eddy current examinations. This method comprises: modeling the eddy current probe using a first numerical method to produce a simulated measurement; modeling the material using a second numerical method to obtain a material model, the second numerical method different from the first numerical method; and simulating the eddy current examination of the material using the simulated measurement and the material model.

Further, the apparatus of the present invention comprises a general purpose computer programmed with software to operate the general purpose computer in accordance with the present invention. In particular the apparatus comprises: means for modeling the eddy current probe using a first numerical method to produce a simulated measurement; means for modeling the material using a second numerical method to obtain a material model, the second numerical method different from the first numerical method; and means for simulating the eddy current examination of the material using the simulated measurement and the material model.

Still further, the article of manufacture of the present invention comprises a computer-readable medium embodying a computer program. For the present invention, the computer-readable medium embodying a computer program comprises code segments to control a general purpose computer to perform the procedure of the present invention. Non-limiting examples of a "computer-readable medium" include a magnetic hard disk, a floppy disk, an optical disk, a magnetic tape, a memory chip, and a carrier wave used to carry electronic data. Non-limiting examples of a "carrier wave used to carry electronic data" include means to transmit electronic data, means to receive electronic data, and means to access an electronic network, such as the Internet. Further, non-limiting examples of "code segments" include software, instructions, computer programs, or any means for controlling a general purpose computer.

In particular, the computer-readable medium embodying a computer program comprises: a first code segment for modeling the eddy current probe using a first numerical method to produce a simulated measurement; a second code segment for modeling the material using a second numerical method to obtain a material model, the second numerical method different from the first numerical method; and a third code segment for simulating the eddy current examination of the material using the said simulated measurement and the material model.

Moreover, the above objects and advantages of the present invention are illustrative, and not exhaustive, of those which can be achieved by the present invention. Thus, these and other objects and advantages of the present invention will be apparent from the description herein or can be learned from practicing the invention, both as embodied herein and as modified in view of any variations which may be apparent to those skilled in the art.

BRIEF DESCRIPTION OF THE DRAWINGS

The invention will be described in greater detail below by way of reference to the accompanying drawings, wherein.

DETAILED DESCRIPTION OF THE PREFERRED EMBODIMENT

Figure 1:
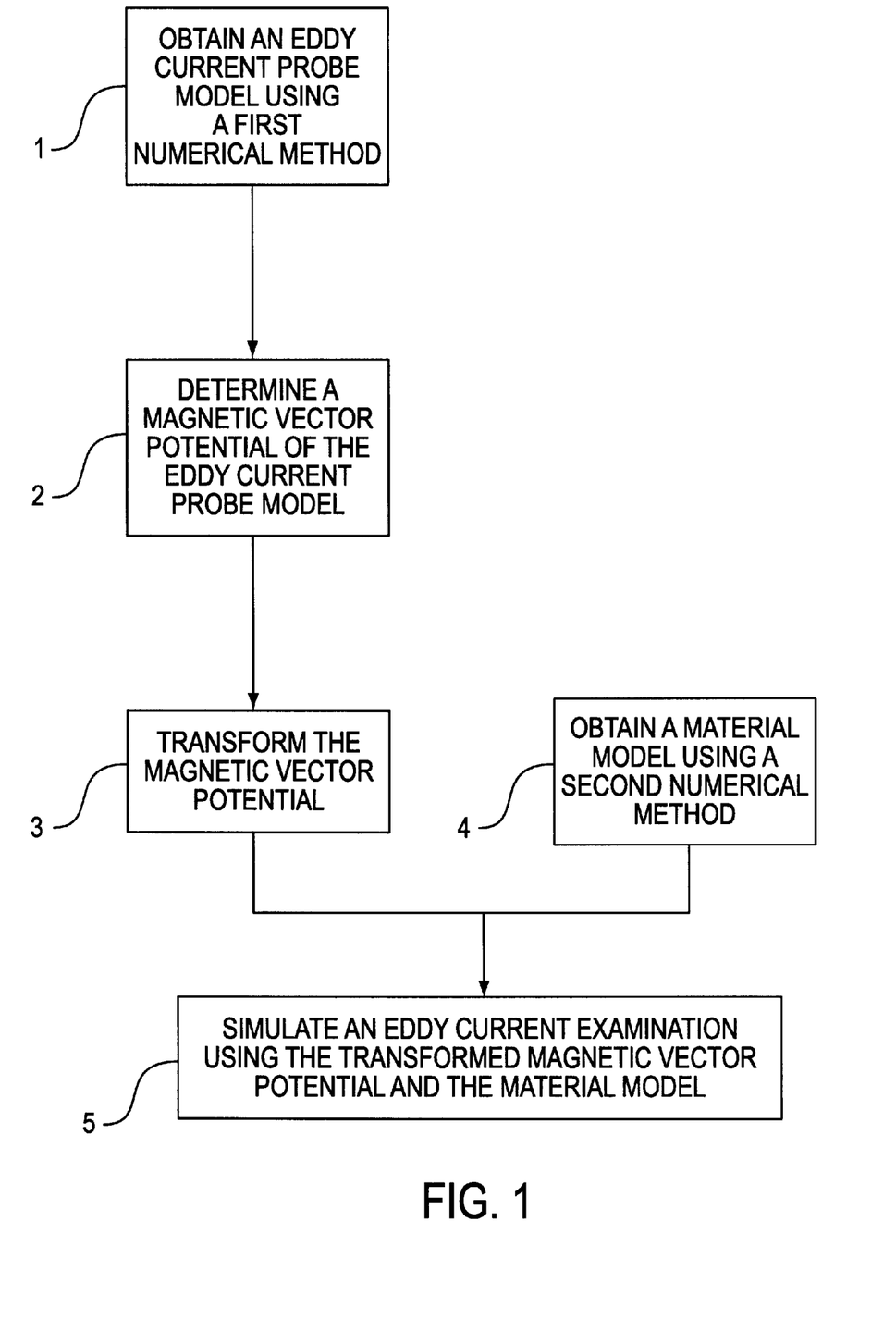
FIG. 1 illustrates the procedure of the preferred embodiment for modeling eddy current probes and simulating eddy current examinations.

Referring now to the accompanying drawings, wherein similar reference characters refer to similar reference parts throughout the drawings, FIG. 1 depicts the procedure used in the preferred embodiment for a method, an apparatus, and an article of manufacture for modeling eddy current probes and simulating eddy current examinations.

In step 1, an eddy current probe model is obtained for at least one eddy current probe using a first numerical method. In the preferred embodiment, the eddy current probe is modeled using the FEM. Alternatively, instead of the FEM, any numerical method which can model the electromagnetic fields for an eddy current probe in air can be used in step 1. Still further, instead of the FEM, any numerical method which can produce a magnetic vector potential pursuant to the interaction between an eddy current probe and a material can be used in step 1.

Further, in step 1, an eddy current probe of any geometry, regardless of its complexity, and of any material can be modeled. Moreover, instead of a single eddy current probe, an array of eddy current probes in any arbitrary configuration can be modeled in step 1. In the present invention, the eddy current probe is modeled in air. Alternatively, the eddy current probe can be modeled in any fluid, such as water. Hence, in step 1, an eddy current probe model of an eddy current probe of any arbitrary geometry, of any complexity, and of any material is produced using a first numerical method.

In step 2, the eddy current probe model of step 1 is used to determine a magnetic vector potential on a plane or surface in space. The magnetic vector potential can be determined for any defined region around the probe. In the present invention, the surface outside the probe is defined, and the magnetic vector potential is determined for points on the surface. Further, this surface may be a plane, cylinder, sphere, or any irregular surface determined by the geometry required for the examination of the material. Hence, in step 2, a magnetic vector potential is produced for a surface using the eddy current probe model of step 1.

In step 3, the magnetic vector potential determined in step 2 is transformed. In the present invention, a variety of transforms can be used, and the choice of which transform to use is dependent upon the surface chosen in step 2. For instance, a two-dimensional Fourier transform, a Hankel transform, or a spherical Hankel transform may be used as dictated by the shape of the surface chosen in step 2. As an example, if a plane is chosen as the shape of the surface in step 2, a two-dimensional Fourier transform can be used in step 3. Hence, in step 3, the magnetic vector potential of step 2 is transformed into a domain useable by a second numerical method, as discussed in step 4.

In step 4, a material model is obtained for a material using a second numerical method, which is different from the first numerical method used in step 1. In the preferred embodiment, the second numerical method is either the VIM or the BEM. Alternatively, instead of the VIM or the BEM, other numerical methods which can model the electromagnetic properties of a material can be used. In the present invention, the material can be any arbitrary material which can be modeled using the second numerical technique. Further, the material can contain one or more flaws of any arbitrary shape and size capable of being modeled using the second numerical technique. Hence, in step 4, a material model is produced for a material.

In step 5, a simulation of an eddy current examination of the eddy current probe and the material is performed using the transformed magnetic vector potential from step 3 and the material model from step 4. In the preferred embodiment, the transformed magnetic potential is used as input to the VIM or the BEM derived material model. In the preferred embodiment, the output of the simulation is the impedance change of the eddy current probe for every point in the examination. Alternatively, instead of the impedance change, the output of the simulation can be any quantity which describes the interaction between the eddy current probe and the material. In the present invention, the examination can be performed for a single point, a scan comprising a series of points, or a series of scans. Hence, in step 5, the material model of step 4 and the transformed magnetic vector potential of step 3 are used to simulate an eddy current examination.

In practicing the procedure of FIG. 1 as a process, the process is performed according to the steps as described above.

In practicing the procedure of FIG. 1 as an apparatus, a general purpose computer is programmed with software to perform the steps of FIG. 1.

Alternatively, instead of using a single general purpose computer, several general purpose computers can be programmed with software corresponding to the various steps of FIG. 1. In this alternative embodiment, each general purpose computer can be programmed with software for performing separate steps of the procedure of FIG. 1.

In practicing this alternative embodiment, each general purpose computer transfers its results to the other general purpose computers requiring its results. Transferring the results from one general purpose computer to another can be implemented using any technique for transferring data between general purpose computers. Non-limiting examples of transferring data between general purpose computers include: means for transferring electronic data using the file transfer protocol, electronic mail, an electronic bulletin board, an electronic network, and a computer-readable medium; and means for one general purpose computer to write to a computer-readable medium and for another general purpose computer to read from the computer-readable medium.

As an example of this alternative embodiment, if the procedure of FIG. 1 is practiced using two general purpose computers, the first general purpose computer could be programmed to practice steps 1–3, and the second general purpose computer could be programmed to practice steps 4–5. After finishing the procedure in step 3, the first general purpose computer then transfers to the second general purpose computer the transformed magnetic vector potential determined in step 3.

In practicing the procedure in FIG. 1 as an article of manufacture, a computer-readable medium embodies a computer program for controlling a general purpose computer to perform the steps of FIG. 1.

In an alternative embodiment, the computer program can be one or more computer programs embodied on one or more computer-readable mediums, and each computer program may be used to control one or more general purpose computers. As an example of this alternative embodiment, the computer program can be divided into three separate code segments: the first code segment corresponding to steps 1–2; the second code segment corresponding to step 3; and the third code segment corresponding to steps 4–5. Further, each of these three code segments can be performed on a separate general purpose computer. Moreover, the steps of FIG. 1 can be divided into code segments in any manner.

THE FEM-VIM EMBODIMENT

In the FEM-VIM embodiment of the present invention, the FEM is used as the first numerical technique in step 1 of FIG. 1, and the VIM is used as the second numerical technique in step 4 of FIG. 1. In this illustration of the FEM-VIM embodiment, an eddy current probe is modeled in air using the FEM, the magnetic vector potential is determined for a planar surface, and the magnetic vector potential is transformed using the Fourier transform.

Using the reciprocity theorem for the VIM, the impedance change for an eddy current probe due to the presence of a flaw in a material can be determined. See B. A. Auld, F. G. Muennemann, and M. Riaziat, "Quantitative Modeling of Flow Responses in Eddy Current Testing," Chap. 2, in Research Techniques in NDT, vol. VII, ed. R. S. Sharpe (Academic Press, New York, 1984). This impedance change is $$\Delta Z = (\sigma/I^2) \int_V E^0 \cdot E \, dV \quad (1)$$

where $\Delta Z$ is the impedance change of the eddy current probe, $\sigma$ is the material conductivity, I is the current in the eddy current probe, $E^0$ is a vector of the unperturbed field in the material, E is a vector of the field in the flaw of the material, "·" is the dot product, V is the flaw volume, and the integral is over the flaw volume V.

To simulate an examination of the material with the flaw, the integral of equation (1) is determined for every point in the examination. The impedance change $\Delta Z$ depends on the electric field E in the flaw, which is given by the following integral equation $$E(x) = E^0(x) - (2i/\delta^2) \int_V G(x,x') \cdot E(x') dV \quad (2)$$

where x is a point in the flaw volume, x' is the variable of the integral over the flaw volume V, $\delta$ is the skin depth, and i is the square root of $-1$, and G is a Green's tensor. See W. S. Dunbar, "The Volume Integral Method of Eddy Current Modeling," J. Nondestructive Eval., 5:9–14 (1985); D. M. McKirdy, "Recent Improvements to the Application of the Volume Integral Method of Eddy Current Modeling," J. Nondestructive Eval., 8:45–52 (1989).

The discretized form of equation (2) is $$\sum_j M_{ij} e_j = e^0_i \quad (3)$$

where $M_{ij}$ is independent of the eddy current probe geometry, i and j are the indices of the matrix, $e_j$ is the j-th element of the column vector of the electric field E, and $e^0_i$ is the i-th element of the column vector for the unperturbed field in the material $E^0$.

The unperturbed field in the material $E^0$ can be obtained using the theory of eddy currents induced by a coil above a half-space and extending it to two layers. See R. E. Beissner and M. J. Sablik, "Theory of Eddy Currents Induced by a Nonsymmetric Coil Above a Conducting Half-Space," J. Appl. Phys., 56:448–454 (1984). This relationship is $$E^0_x(\rho, z) = -(\omega\mu_0/2\pi) \int_{-\infty}^{\infty} [a_n e^{\lambda_n z} + b_n e^{-\lambda_n z}] e^{ik \cdot (\rho - \rho_0)} k_y \hat{z} \cdot k \times a_s^0 d^2k \quad (4)$$

$$E^0_y(\rho, z) = (\omega\mu_0/2\pi) \int_{-\infty}^{\infty} [a_n e^{\lambda_n z} + b_n e^{-\lambda_n z}] e^{ik \cdot (\rho - \rho_0)} k_x \hat{z} \cdot k \times a_s^0 d^2k \quad (5)$$

$$E^0_z = 0 \quad (6)$$

where $\rho$ is a vector of the cylindrical coordinates of the eddy current probe in the x-y plane; z is the vertical coordinate of the cylindrical coordinates of the eddy current probe, $\rho_0$ are the cylindrical coordinates for the center of the eddy current probe, $\omega$ is $2\pi f$, f is the frequency of excitation of the alternating field, $\mu_0$ is the permeability of free space, which is $4\pi \times 10^{-7}$ Tesla meters/Ampere-turns, n is either 1 or 2 and denotes the layer number, k is $k_x \hat{x} + k_y \hat{y}$, $\hat{x}$ and $\hat{y}$ are the unit vectors in the x-y plane, $\hat{z}$ is the unit vector in the vertical direction, $a_s^0$ is the Fourier transform of the magnetic vector potential $A^0$, "×" is the cross product, and the integral is from $-\infty$ to $+\infty$ for $d^2k$ equal to $dk_x dk_y$. Further, $$a_2 = (4i\lambda_1/\mu_0 k)/[(e_2/e_1)(k+\lambda_1)(\lambda_2+\lambda_1) - e_2 e_1 (k-\lambda_1)(\lambda_2-\lambda_1)] \quad (7)$$

$$b_2 = 0 \tag{8}$$

$$a_1 = (e_2/2e_1)[1+(\lambda_2/\lambda_1)]a_2 \tag{9}$$

$$b_1 = (e_2e_1/2)[1-(\lambda_2/\lambda_1)]a_2 \tag{10}$$

$$q_n^2 = i\omega\mu_0\sigma_n \tag{11}$$

$$\lambda_n = (k^2 - \rho_n^{\ 2})^{0.5} \tag{12}$$

$$e_n = e^{80 \ n \neq 1} \tag{13}$$

where $\sigma_n$ is the conductivity of the n-th layer, $\lambda_1$ and $\lambda_2$ are the positive square roots of equation (12), and $z_1$ in equation (11) is the coordinate of the interface between the first and second layers of the material.

Because the surface as determined in step 2 in this FEM-VIM embodiment is a plane, $a_s^0$ is the Fourier transform determined in step 3 of the magnetic vector potential $A^0$ of the plane surface determined in step 2.

As can be appreciated by one skilled in the art, $E^0$ depends on the magnetic vector potential $A^0$ of the eddy current probe, the material conductivity $\sigma$, and the skin depth $\delta$. With the present invention, the geometry of the eddy current probe is not coupled to the geometry of the material or the flaw. In particular, the flaw determines M, and the eddy current probe determines $E^0$. In practicing the present invention, these two quantities can be determined independently of each other. Hence, the examination of the material is generated by determining the impedance change $\Delta Z$ of the eddy current probe model using M and Eo for each point in the examination.

THE FEM-BEM EMBODIMENT

In the FEM-BEM embodiment of the present invention, the FEM is used as the first numerical technique in step 1 of FIG. 1, and the BEM is used as the second numerical technique in step 4 of FIG. 1. In this illustration of the FEM-BEM embodiment, an eddy current probe is modeled in air using the FEM, the magnetic vector potential is determined for a planar surface, and the magnetic vector potential is transformed using the Fourier transform.

The impedance change for an eddy current probe due to the presence of a flaw in a material is $$\Delta Z = (i\omega\mu_0/I^2)\int_s[(\Phi(d\Phi_0/dn) - \Phi_0(d\Phi/dn)]dS \tag{14}$$

where $\Delta Z$ is the impedance change of the eddy current probe, i is the square root of $-1$, $\omega$ is $2\pi f$, f is the frequency of excitation of the alternating field, $\mu_0$ is the permeability of free space, which is $4\pi \times 10^{-7}$ Tesla meters/Ampere-turns, $\Phi$ is the magnetic scalar potential, $\Phi_0$ is the magnetic scalar potential in free space and is a continuous function of position, d/dn is the first derivative where n is normal to the surface of the material, S is the surface of the material and flaw, and the integral is over the surface S. Further, the magnetic scalar potential $\Phi$ is defined by $$H = -\nabla\Phi \tag{15}$$

where H is magnetic field strength and $\nabla\Phi$ is the gradient of the magnetic scalar potential $\Phi$.

To simulate an examination of the material with the flaw, the integral of equation (14) is determined for every point in the examination. The impedance change $\Delta Z$ depends on the scalar potential $\Phi$ at the flaw surface, which is the solution of the following boundary integral equation $$\Phi(x) = \Phi_0(x) - \int_s[G_0(x,x')(d\Phi(x')/dn) - (\Phi(x') - \Phi(x))(G_0(x,x')/dn)]dS \tag{16}$$

where x is a point on the flaw surface, x' is the variable of the integral over the flaw surface, and the integral is over the material and flaw surface S. Further, $$G_0(x,x') = (1/4\pi|x-x'|) \tag{17}$$

where $|x|$ is the absolute value of x.

The discretized form of equation (16) is $$\sum_j M_{ij}\Phi_j = \Phi_i^0 \tag{18}$$

where $M_{ij}$ is independent of the eddy current probe geometry, i and j are the indices of the matrix, $\Phi_j$ is the j-th element of the column vector of the magnetic scalar potential $\Phi$, and $\Phi_i^0$ is the value of the magnetic scalar potential in free space $\Phi_0$ at the i-th point on the surface.

The relationship between the magnetic scalar potential $\Phi$ and the magnetic vector potential $A^0$ for a coil in air is given by $$\Phi(\rho, z) = -(i/2\pi\mu_0)\int_{-\infty}^{\infty}(1/k)e^{ik\cdot\rho}\hat{z}\cdot k \times a_s^0 d^2k \tag{19}$$

where $\rho$ is a vector of the cylindrical coordinates of the eddy current probe in the x-y plane, z is the vertical coordinate of the cylindrical coordinates of the eddy current probe, k is the magnitude of k, k is $k_x \hat{x} + k_y \hat{y}$, $\hat{x}$ and $\hat{y}$ are the unit vectors in the x-y plane, $\hat{z}$ is the unit vector in the vertical direction, $a_s^0$ is the Fourier transform of the magnetic vector potential $A^0$, "·" is the dot product, "x" is the cross product, and the integral is from $-\infty$ to $+\infty$ for $d^2k$ equal to $dk_x dk_y$.

Because the surface as determined in step 3 in this FEM-BEM embodiment is a plane, $a_s^0$ is the Fourier transform determined in step 3 of the magnetic vector potential $A^0$ of the plane surface determined in step 2.

As can be appreciated by one skilled in the art, $\Phi_0$ depends on the magnetic vector potential $A^0$ of the eddy current probe. With the present invention, the geometry of the eddy current probe is not coupled to the geometry of the material or the flaw. In particular, the flaw determines M, and the eddy current probe determines $\Phi_0$. In practicing the present invention, these two quantities can be determined independently of each other. Hence, the examination of the material is generated by determining the impedance change $\Delta Z$ of the eddy current probe model using M and $\Phi_0$ for each point in the examination.

EXAMPLE OF THE FEM-VIM EMBODIMENT

Figure 2:
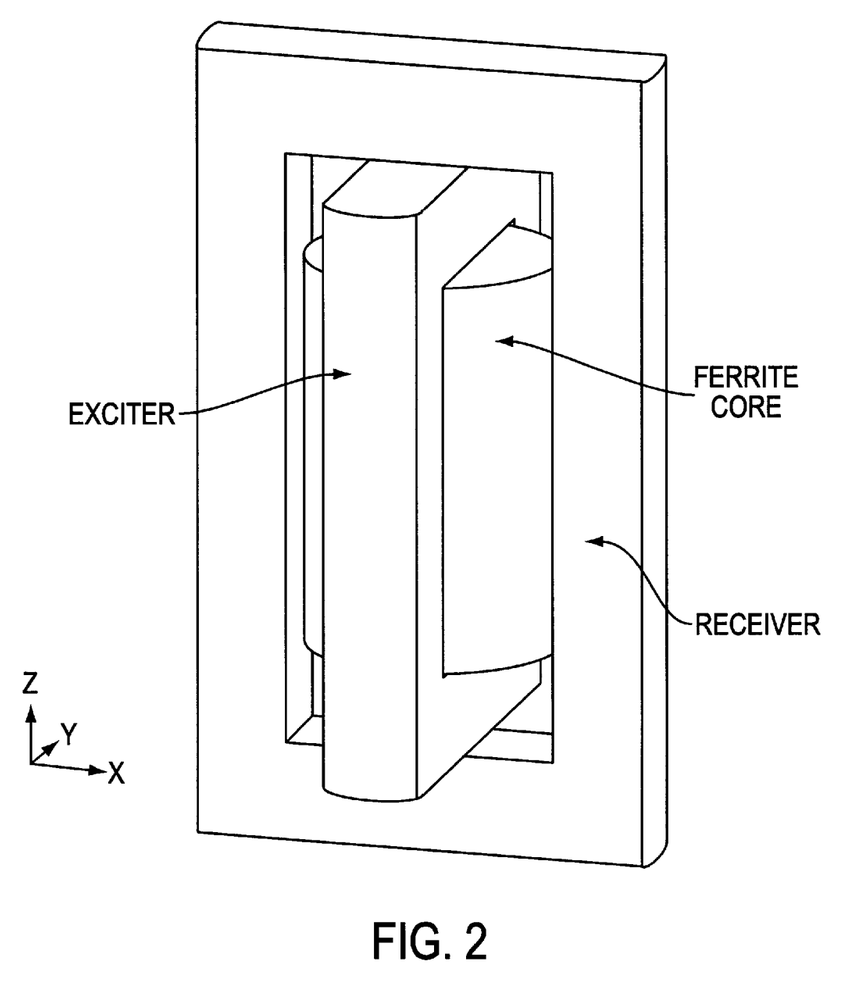
FIG. 2 illustrates an eddy current probe modeled using the FEM.

In this example of the FEM-VIM embodiment, simulated and experimental results are compared for an eddy current examination of a piece of stainless steel with a flaw using a cross-axis eddy current probe developed by the Southwest Research Institute, San Antonio, Tex. For the eddy current probe, separate exciter and receiver coils are wound around a cylindrical ferrite core, which is shown in FIG. 2. Because of the rectangular windings and the ferrite core, the eddy current probe is easily modeled using the FEM.

The eddy current probe is approximately 11 mm in outside diameter by 20 mm in axial height. The ferrite core is 6 mm in diameter by 10 mm in axial height. The current was 50 Ampere-turns at 30 kHz. The eddy current probe was scanned across stainless steel, which has a conductivity of $\sigma = 1.45 \times 10^6$ S/m, and which has a surface-breaking notch approximately 10 mm in length by 0.2 mm in width by 2.0 mm in depth.

Figure 3:
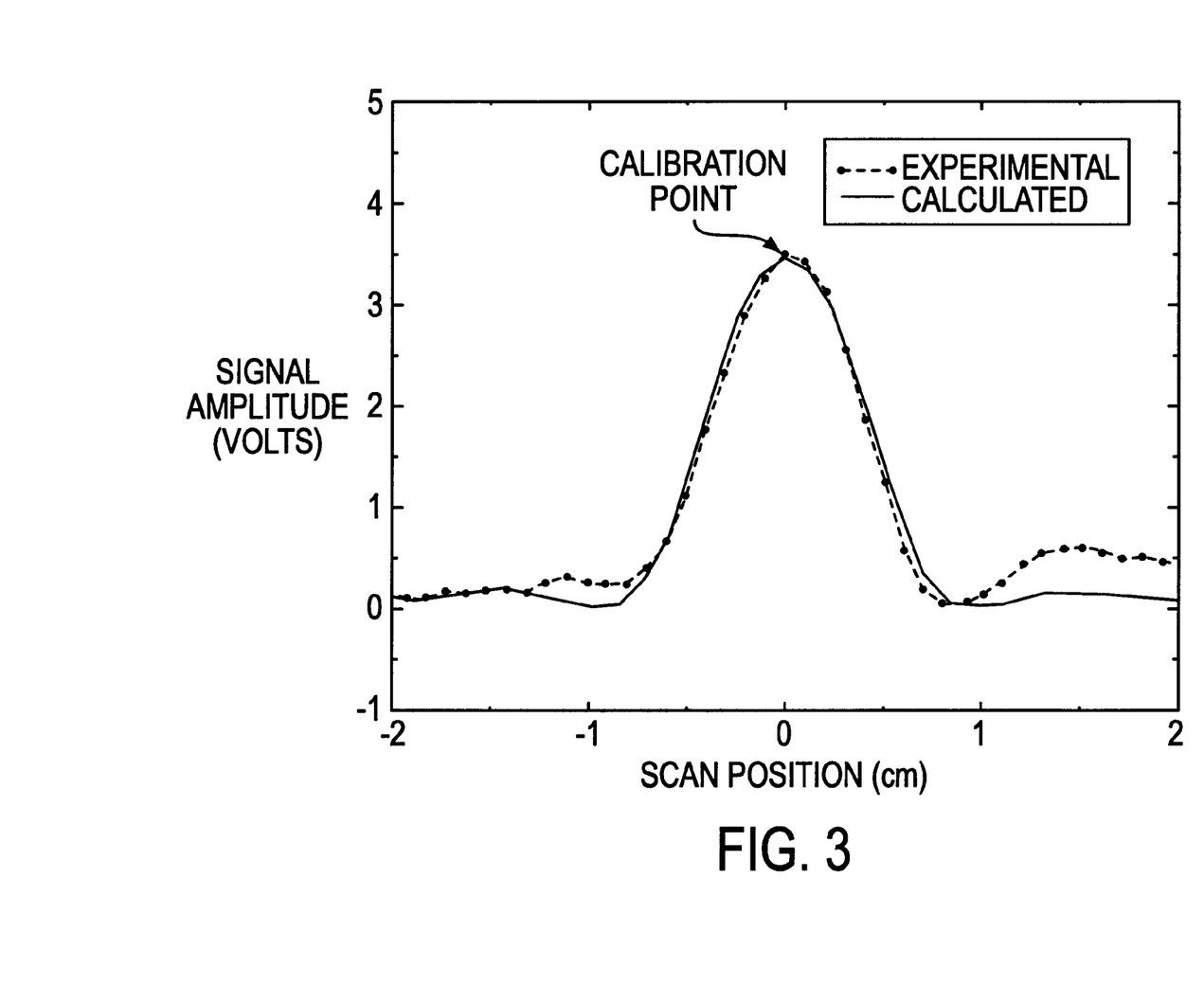
FIG. 3 compares the real component of the complex voltage change for the eddy current probe of FIG. 2 obtained from a scan across a flaw using the FEM-VIM embodiment with that obtained using the same probe experimentally.
Figure 4:
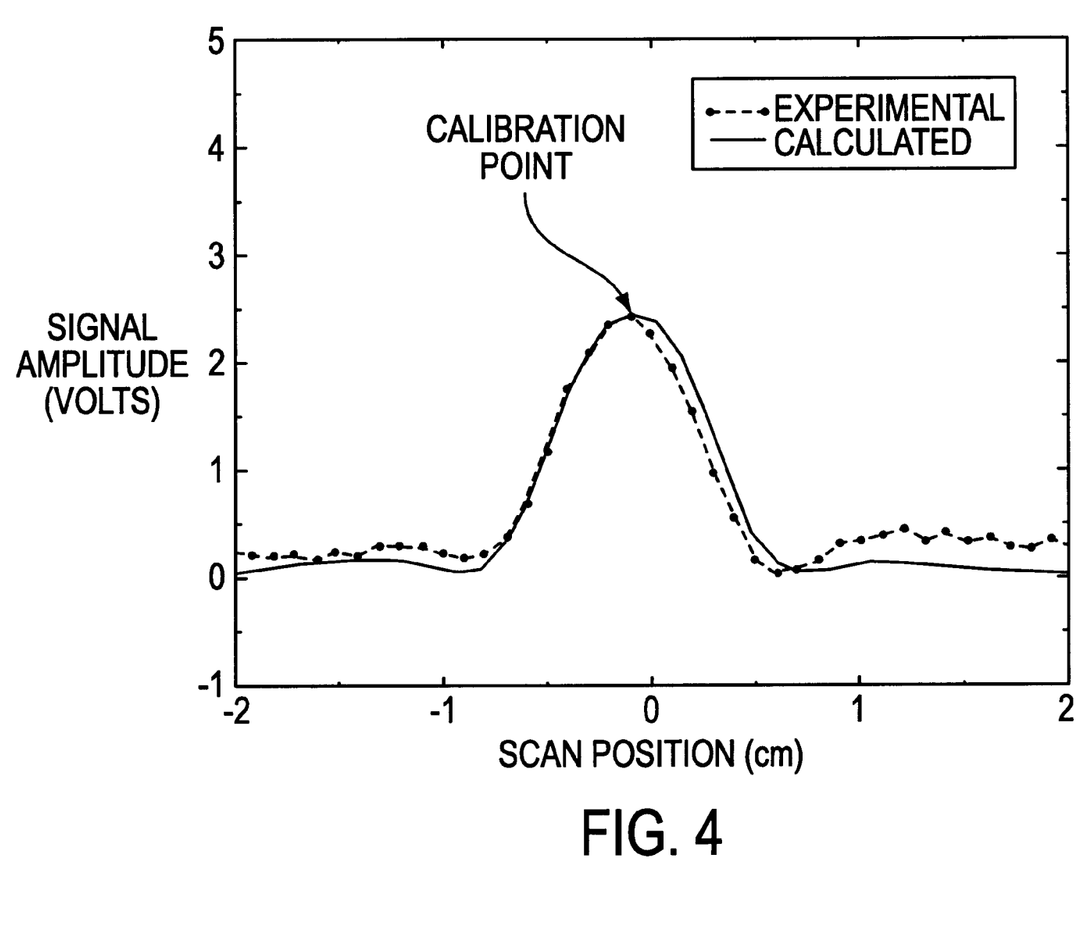
FIG. 4 compares the imaginary component of the complex voltage change for the eddy current probe of FIG. 2 obtained from a scan across a flaw using the FEM-VIM embodiment with that obtained using the same probe experimentally.

Using the procedure in FIG. 1, an examination of the material was simulated where the first numerical method was the FEM, and the second numerical method was the VIM. The results from a simulated examination and a corresponding experimental examination are compared in FIGS. 3 and 4. FIG. 3 shows the real component of the eddy current probe complex voltage change, which is proportional to the output impedance change, for a scan across the flaw. FIG. 4 shows the imaginary component of the eddy current probe complex voltage change, which is proportional to the output impedance change, for the same scan. In FIGS. 3 and 4, the peak value of the simulated voltage change was calibrated to match the experimental voltage change by rotating the phase and scaling the amplitude. This impedance plane rotation and scaling was applied to all points of the scan.

Figure 5:
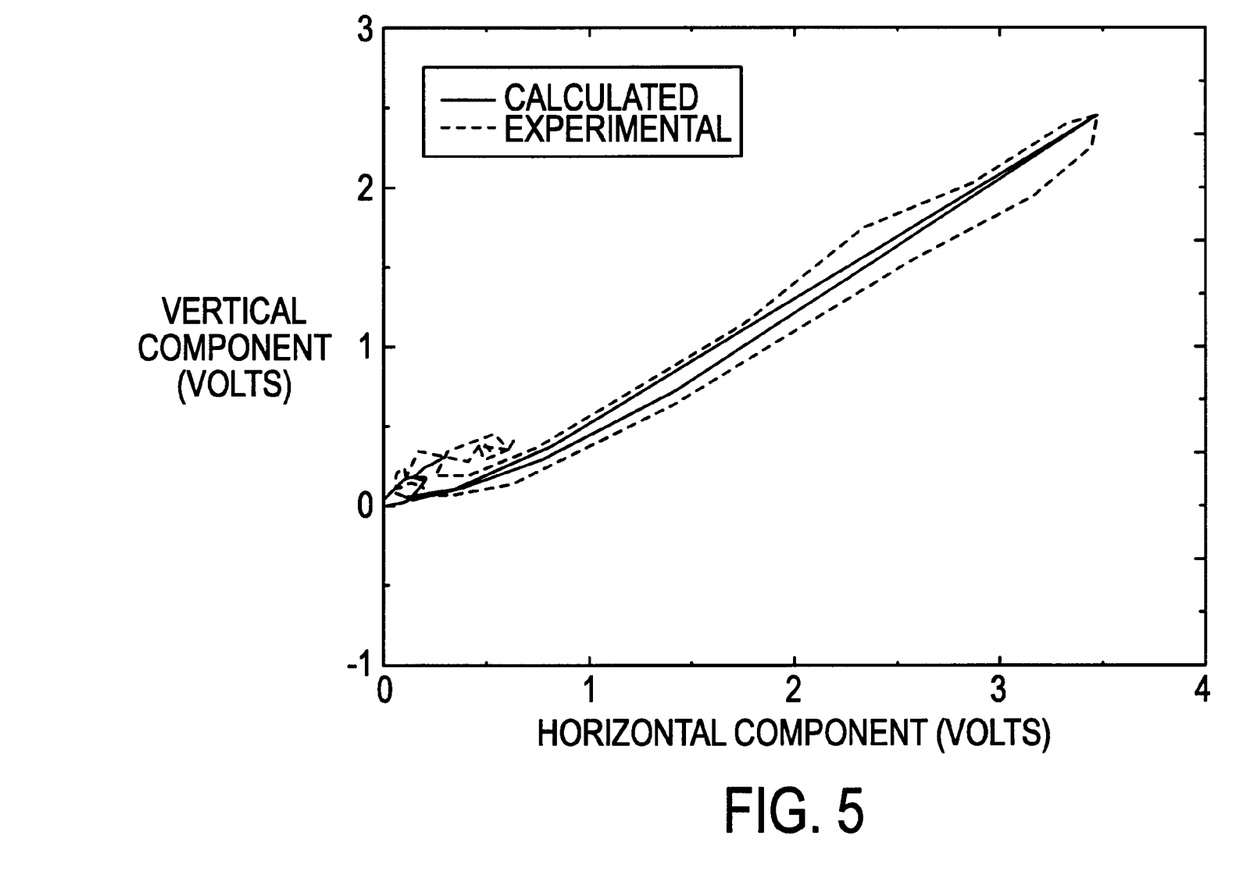
FIG. 5 compares the impedance plane signal from the eddy current probe of FIG. 2 obtained using the FEM-VIM embodiment with that obtained experimentally.

In FIG. 5, a comparison of the output impedance plane signal is shown. The amplitude and the phase in FIG. 5 of the simulated voltage change were calibrated to match the experimental voltage change at one point, namely the peak, in the scan. The experimental voltage changes differ in the amount of current used for the excitation, and also in the gain applied to the receiver signal. In addition, the experimental eddy current probe has a ferrite shield around it, and the simulated eddy current probe did not. For these reasons, the results in FIG. 5 are compared qualitatively. As can be seen in FIGS. 3–5, the relative amplitudes of the horizontal and vertical components are similar, and the shapes of the signals are the same.

The invention has been described in detail with respect to preferred embodiments, and it will now be apparent from the foregoing to those skilled in the art that changes and modifications may be made without departing from the invention in its broader aspects, and the invention, therefore, as defined in the appended claims is intended to cover all such changes and modifications as fall within the true spirit of the invention.

What is claimed is:

1. A process for simulating an eddy current measurement of a material using an eddy current probe, comprising:

modeling said eddy current probe using a first numerical method to produce a simulated measurement;

modeling said material using a second numerical method to obtain a material model, said second numerical method being different from said first numerical method; and simulating the eddy current examination of said material using said simulated measurement and said material model.

2. A process for simulating an eddy current measurement of a material using an eddy current probe as in claim 1, wherein said first numerical method is a finite element method, and said second numerical method is a volume integral method.

3. A process for simulating an eddy current measurement of a material using an eddy current probe as in claim 1, wherein said first numerical method is a finite element method, and said second numerical method is a boundary element method.

4. A process for simulating an eddy current measurement of a material using an eddy current probe as in claim 1, wherein the step of modeling said eddy current probe comprises:

determining a magnetic vector potential for a surface.

5. A process for simulating an eddy current measurement of a material using an eddy current probe as in claim 4, wherein the step of modeling said eddy current probe further comprises:

transforming said magnetic vector potential to obtain said simulated measurement.

6. A process for simulating eddy current measurements of a material using an eddy current probe as in claim 1, wherein the step of simulating the eddy current examination comprises:

determining said eddy current examination for a plurality of points.

7. An apparatus for simulating an eddy current examination of a material using an eddy current probe, comprising:

means for modeling said eddy current probe using a first numerical method to produce a simulated measurement;

means for modeling said material using a second numerical method to obtain a material model, said second numerical method being different from said first numerical method; and means for simulating the eddy current examination of said material using said simulated measurement and said material model.

8. An apparatus for simulating an eddy current examination of a material using an eddy current probe as in claim 7, wherein said first numerical method is a finite element method, and said second numerical method is a volume integral method.

9. An apparatus for simulating an eddy current examination of a material using an eddy current probe as in claim 7, wherein said first numerical method is a finite element method, and said second numerical method is a boundary element method.

10. A computer-readable medium embodying a computer program for simulating an eddy current examination of a material using an eddy current probe, comprising:

a first code segment for modeling said eddy current probe using a first numerical method to produce a simulated measurement;

a second code segment for modeling said material using a second numerical method to obtain a material model, said second numerical method being different from said first numerical method; and a third code segment for simulating the eddy current examination of said material using said simulated measurement and said material model.

11. A computer-readable medium embodying a computer program for simulating an eddy current examination of a material using an eddy current probe as in claim 10, wherein said first numerical method is a finite element method, and said second numerical method is a volume integral method.

12. A computer-readable medium embodying a computer program for simulating an eddy current examination of a material using an eddy current probe as in claim 10, wherein said first numerical method is a finite element method, and said second numerical method is a boundary element method.

13. A process for simulating an eddy current measurement of a material using an eddy current probe, comprising:

modeling said eddy current probe using a first numerical method to obtain an eddy current probe model;

determining a magnetic vector potential of said eddy current probe model;

transforming said magnetic vector potential to obtain a transformed magnetic potential;

modeling said material using a second numerical method to obtain a material model, said second numerical method being different from said first method; and determining a measurement for said eddy current probe model using said transformed magnetic vector potential and said material model, thereby simulating the eddy current measurement of said material.

14. A process for simulating eddy current measurements of a material using at least one eddy current probe as in claim 13, wherein said first numerical method is a finite element method, and said second numerical method is a volume integral method.

15. A process for simulating eddy current measurements of a material using at least one eddy current probe as in claim 13, wherein said first numerical method is a finite element method, and said second numerical method is a boundary element method.

* * * * *